United States Patent [19]
Näf et al.
[11] 4,266,075
[45] May 5, 1981

[54] BICYCLIC ALDEHYDE DERIVATIVES, THEIR USE AS PERFUMING AND FLAVORING INGREDIENTS AND PROCESS FOR THEIR PREPARATION

[75] Inventors: Ferdinand Näf, Geneva; René Decorzant, Onex, both of Switzerland

[73] Assignee: Firmenich, S.A., Geneva, Switzerland

[21] Appl. No.: 95,201

[22] Filed: Nov. 19, 1979

Related U.S. Application Data

[62] Division of Ser. No. 940,836, Sep. 8, 1978, Pat. No. 4,218,347.

[30] Foreign Application Priority Data

| | | | |
|---|---|---|---|
| Sep. 15, 1977 | [CH] | Switzerland | 78234/77 |
| Oct. 3, 1977 | [CH] | Switzerland | 11281/77 |

[51] Int. Cl.[3] .......... C07C 69/74
[52] U.S. Cl. .......... 560/120; 560/118
[58] Field of Search .......... 560/118, 120

[56] References Cited

U.S. PATENT DOCUMENTS

| | | | |
|---|---|---|---|
| 3,053,882 | 9/1962 | Miller | 560/120 |
| 3,673,261 | 6/1972 | Kretschmar | 560/120 |

OTHER PUBLICATIONS

Chem. Absts. vol. 66, No. 54755F (1967).

*Primary Examiner*—John F. Niebling
*Attorney, Agent, or Firm*—Scully, Scott, Murphy & Presser

[57] ABSTRACT

Bicyclic aldehyde derivatives of formula

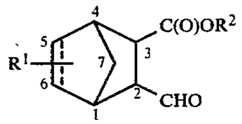

(I)

containing a single or a double bond in the position indicated by the dotted lines and wherein symbol $R^1$ represents a hydrogen atom or a methyl radical and $R^2$ defines a linear or branched alkyl radical containing 1 to 6 carbon atoms.

Compounds (I) find specific utility as perfuming and flavoring agents.

Process for the preparation of said compounds (I) starting from cyclopentadiene or a methyl substituted cyclopentadiene and an alkyl 4-oxo-butenoate.

3 Claims, No Drawings

BICYCLIC ALDEHYDE DERIVATIVES, THEIR USE AS PERFUMING AND FLAVORING INGREDIENTS AND PROCESS FOR THEIR PREPARATION

This is a division of application Ser. No. 940,836, filed Sept. 8, 1978, now U.S. Pat. No. 4,218,347.

THE INVENTION

The invention relates to the use of a new class of bicyclic aldehyde derivatives of formula (I). Specifically, the invention is concerned with a process for improving, modifying or enhancing the organoleptic properties of perfumes and perfumed products, as well as of foodstuffs, beverages, pharmaceutical preparations and tobacco products, which process comprises the step of adding thereto an effective amount of at least one of the compounds of formula (I).

The invention relates further to a flavouring or perfuming composition which comprises having added thereto an effective amount of at least one of the compounds of formula (I). The invention relates also to a perfume, a perfumed product, a foodstuff, a beverage, a pharmaceutical preparation or a tobacco product which comprises having added thereto a perfuming or flavouring effective amount of at least one of the compounds of formula (I).

A further object of the present invention consists in a process for preparing said compounds of formula (I), which comprises reacting in the presence of an inert organic solvent a compound of formula $OCH—CH=CH—C(O)OR^2$ (II)

wherein symbol $R^2$ is defined as indicated above with a cyclopentadiene derivative of formula (III)

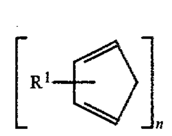

wherein index n defines integer 1 or 2 and symbol $R^1$ is defined as above, to give the compound of formula (I) comprising a double bond at the position indicated by the dotted lines, and subjecting the thus obtained compound to a catalytic hydrogenation to obtain its corresponding saturated derivative.

BACKGROUND OF THE INVENTION

In spite of the already existing great variety of flavourants and perfuming ingredients which are presently at the disposal of perfumes and flavourists, there still exist extended gaps in certain area of the art. For instance, so far perfumers do not dispose of odorous compounds enabling the faithful reproduction of the typical fruity note of melon. Though certain compounds have been used in the past for that purpose, their utilization was not fully satisfactory in all practical cases encountered; none of those prior known compounds possessed in fact a pure melon character, free of unpleasant fatty off-odours.

We have surprisingly found that by the use of the compounds of formula (I), especially of those compounds of formula (I) which contain a double bond in the position indicated by the dotted line, it was possible to develop unprecedented fruity odorous notes of melon character which character was not accompanied by unpleasant off-odours. Consequently, the said compounds are particularly appreciated for their possibilities in modern perfumery compounding.

PREFERRED EMBODIMENTS OF THE INVENTION

With the exception of methyl 2-formyl-bicyclo[2.2.1]hept-5-en-3-yl-carboxylate (formula (I) wherein $R^1=H$ and $R^2=CH_3$) compounds (I) are novel compositions of matter. The above said methyl ester has been described in Chem.Abstr., 66, 54755 f (1966), however no mention nor suggestion has been formulated therein concerning its possible use in the fields of perfumery or flavours, neither is there any description relative to its organoleptic properties. Compounds (I) are obtained according to a novel process which consists in reacting an aldehydic ester of formula (II) with a cyclopentadiene derivative of formula (III).

This reaction is effected in the presence of an inert organic solvent according to the conditions normally used for carrying out a Diels-Alder cyclo-addition [see e.g.: H.O. House, Modern Synthetic Reactions, W. A. Benjamin Inc. (1972), p. 817]. Suitable inert organic solvents include an ether such as diethyl ether, tetrahydrofuran or dioxane, a hydrocarbon such as hexane or cyclohexane, or an aromatic hydrocarbon such as benzene or toluene. The reaction can be carried out at atmospheric pressure or at a pressure higher than this one. By operating at atmospheric pressure the reaction temperature is generally chosen in the vicinity of the boiling point of the selected solvent; whereas by effecting the reaction in a closed vessel, such as an autoclave, the temperature used can be of the order of about 150° to 250° C., and the operative pressure of about 15 to 150 atmospheres.

Optionally, the reaction is carried out in an atmosphere of inert gas; to this effect nitrogen, argon and helium can conveniently be used. Moreover, in accordance with a preferred embodiment of the present invention, better yields of the desired end-products are obtained by making use of inhibitors of polymerization, e.g. hydroquinone or pyrogallol.

As stated above, the subsequent conversion of the compounds of formula (I), containing a double bond in the position indicated by the dotted lines, into their corresponding saturated derivatives is effected by catalytic hydrogenation. The current techniques are used to this end. Suitable metal catalysts are selected among Raney-nickel, palladium on charcoal and platinum oxide.

Typical examples of the compounds of formula (I) which can be prepared in accordance with the invention process include:

ethyl 2-formyl-bicyclo[2.2.1]hept-5-en-3-yl-carboxylate, isopropyl 2-formyl-bicyclo[2.2.1]hept-5-en-3-yl-carboxylate, n-propyl 2-formyl-bicyclo[2.2.1]hept-5-en-3-yl-carboxylate, n-butyl 2-formyl-bicyclo[2.2.1]hept-5-en-3-yl-carboxylate, sec-butyl 2-formyl-bicyclo[2.2.1]hept-5-en-3-yl-carboxylate, n-pentyl 2-formyl-bicyclo[2.2.1]hept-5-en-3-yl-carboxylate, ethyl 5-methyl-2-formyl-bicyclo[2.2.1]hept-5-en-3-yl-carboxylate and ethyl 6-methyl-2-formyl-bicyclo[2.2.1]hept-5-en-3-carboxylate.

Owing to their particular molecular structure, compounds (I) can occur under one of the following stereoisomeric forms (as illustrated hereinbelow for ethyl 2-formyl-bicyclo[2.2.1]hept-5-en-3-yl-carboxylate):

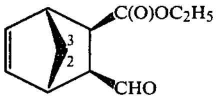

2-endo, 3-endo

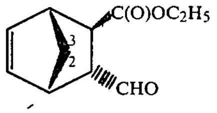

2-exo, 3-endo

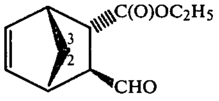

2-endo, 3-exo

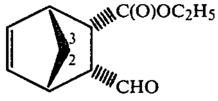

2-exo, 3-exo

However, for practical and economical reasons, the compounds obtained in accordance with the described process are utilized as such without preliminary separation of the single isomeric entities.

Compounds of formula (II), used as starting materials in the invention process, can be readily synthetized in accordance with known processes, e.g. in accordance with the procedure described in Tetrahedron Letters 1972, 3777 and 1973, 2417, whereas cyclopentadiene and methyl-cyclopentadiene ($R^1$=H and $CH_3$, respectively, in formula III) are commercially available products which can be utilized under their monomeric or dimeric form (n=1, or 2, respectively in formula III) depending on the type of reaction vessel as well as on the reaction conditions chosen.

The particular utility of the compounds of formula (I) in the area of perfumery is not limited to the reproduction of melon notes, they can also be used for improving advantageously odorous notes as various as the fruity, flowery and green notes. These characters are reminiscent of the odour developed by water melon or cucumber.

Owing to their useful properties, compounds (I) can be used in a wide range of applications both in fine and technical perfumery. Thus compounds (I) can be used as ingredients for the manufacture of perfume compositions, perfume bases and concentrates as well as for the perfuming of products such as soaps, detergents, cosmetics or household materials. Moreover, they can be used on their own or in admixture with other perfuming ingredients, solvents or substrates. The range of concentrations can vary from about 0.1 to 30% by weight of the total weight of the compositions into which they are incorporated; a preferred range is of between about 1 and 20%. Concentrations higher or lower than the above given limits can be used whenever special effects are desired, namely in the manufacture of perfume bases and concentrates.

In the field of flavours, compounds (I) are characterized by a fruity note clearly reminiscent of that of melon or of exotic fruits, such as e.g. papaya. Consequently, compounds (I) can be used for the manufacture of artificial flavours of fruit type and for the aromatization of foodstuffs such as ice-creams, creams, jellies, yoghourts, candies or chewing-gums for example, of beverages such as syrups, of pharmaceutical preparations and of tobacco products.

In the fields of flavours, the compounds of formula (I) can be used at concentrations of between about 0.01 and 20 ppm (parts per million) by weight. Preferred concentrations are of between about 0.1 and 10 ppm. These values depend of course on the nature of the products into which compounds (I) are incorporated and on the nature of the coingredients in a given composition.

The invention is better illustrated by but not limited to the following examples wherein the temperatures are indicated in degrees centrigrade.

EXAMPLE 1

Ethyl 2-formyl-bicyclo[2.2.1]hept-5-en-3-yl-carboxylate

Method A: A solution of 128 g (1.0 mole) of ethyl 4-oxo-butenoate in 200 ml of diethyl ether has been placed in a 1000 ml flask equipped with a reflux condenser, an introductory funnel and a stirrer, and, after having been cooled to 15°, the said solution was added of 79.2 g (1.2 mole) of freshly distilled cyclopentadiene in 100 ml of diethyl ether. During the addition of the reactants the temperature of the reaction mixture was kept at 15° by external cooling, then, once the addition was over, the temperature was increased to the boiling point and kept at this value for 2 h.

After taking off of the volatile fractions under reduced pressure and distillation of the residue over a Vigreux column there was isolated a product having b.p. 77°-8°/0.1 Torr (166 g, yield 85%).

IR: 3070, 2820, 2720, 1740-1710, 1570 $cm^{-1}$;

NMR: (60 MHz): 1.1-1.7 (5H); 2.8 (1H); 3.2-3.5 (3H); 4.12 and 4.20 (2H, 2q, J=7.5 Hz); 6.1-6.4 (2H); 9.58 and 9.88 (1H, 2s) δ ppm;

MS: m/e=165 (6), 149 (8), 129 (10), 121 (25), 103 (4), 91 (19), 83 (34), 66 (100), 55 (19), 39 (21), 27 (25).

Another sample of the same product was analyzed by NMR by making use of a 90 MHz apparatus. Here is reproduced the obtained spectrum:

NMR: 1.23 and 1.28 (3H, 2t, J=7.5 Hz); 1.35-1.83 (2H); 2.65-2.95 (1H); 3.15-3.53 (3H); 4.12 and 4.20 (2H, 2q, J=7.5 Hz); 6.03-6.43 (2H); 9.58 and 9.88 (1H, 2s) δ ppm.

The product obtained in accordance with the above described procedure consisted in a mixture of isomers as indicated by the pairs of signals at 9.58 and 4.12, and respectively at 9.88 and 4.20 ppm. For practical reasons the thus obtained isomeric mixture is used as such without further purification.

Method B: 7.2 g (0.11 mole) of dicyclopentadiene, 14.2 g (0.10 mole) of ethyl 4-oxo-butenoate and 0.1 g of hydroquinone dissolved in 90 ml of toluene were introduced in a glass tube destined to be used for reactions under pressure (φ2 cm—length 60 cm). A flow of argon was bubbled through the solution during 10 min., whereupon the tube was sealed and finally brought to 200° (external temperature) and kept at this temperature for 2 h. After cooling and taking off of the volatile fractions under reduced pressure there was obtained a residue which upon distillation on a Vigreux column gave 11.4 g (yield 59%) of the desired product (b.p. 62°-4°/0.04 Torr).

According to analysis, the product obtained was identical to that prepared in accordance with method A above.

EXAMPLE 2

By substituting an homologous ester for ethyl 4-oxobutenoate and by following the same procedure as that indicated in Example 1 above, the following compounds were synthesized:

n-propyl 2-formyl-bicyclo[2.2.1]hept-5-en-3-yl-carboxylate b.p. 76°-80°/0.1 Torr.

IR: 3060, 2820, 2720, 1735–1715, 1570 $cm^{-1}$.

NMR: 0.96 (3H, t, J=7 Hz); 1.2–2.0 (4H); 2.8 (1H); 3.24–3.56 (3H); 2.02 and 2.10 (2H, 2t, J=7 Hz); 6.02–6.44 (2H); 9.60 and 9.90 (1H, 2s) δppm.

isopropyl 2-formyl-bicyclo[2.2.1]hept-5-en-3-yl-carboxylate b.p. 73°-4°/0.1 Torr.

NMR: 1.20 and 1.24 (6H, 2d, J=6 Hz); 1.10–1.83 (2H); 2.60–2.88 (1H); 3.12–3.48 (3H); 4.73–5.28 (1H, m); 6.01–6.42 (2H); 9.58 and 9.88 (1H, 2s) δ ppm.

n-butyl 2-formyl-bicyclo[2.2.1]hept-5-en-3-yl-carboxylate

NMR: 0.94 (3H, t, J=6 Hz); 1.20–1.96 (6H); 2.65–2.92 (1H); 3.16–3.57 (3H); 4.08 and 4.13 (2H, 2t, J=6.5 Hz); 6.02–6.43 (2H); 9.59 and 9.89 (1H, 2s) δ ppm.

sec-butyl 2-formyl-bicyclo[2.2.1]hept-5-en-3-yl-carboxylate b.p. 80°-2°/0.1 Torr.

NMR: 0.90 (3H, t, J=7.5 Hz); 1.19 and 1.22 (3H, 2d, J=6 Hz); 1.30–1.90 (4H); 2.65–2.96 (1H); 3.15–3.57 (3H); 4.65–5.18 (1H, m); 6.02–6.45 (2H); 9.60 and 9.90 (1H, 2s) δ ppm.

n-pentyl 2-formyl-bicyclo[2.2.1]hept-5-en-3-yl-carboxylate b.p. 99°-102°/0.1 Torr.

NMR: 0.92 (3H, t, J=5 Hz); 1.18–2.07 (8H); 2.68–2.93 (1H); 3.18–3.68 (3H); 4.08 and 4.14 (2H, t, J=6 Hz); 6.05–6.45 (2H); 9.61 and 9.91 (1H, 2s) δ ppm.

methyl 2-formyl-bicyclo[2.2.1]hept-5-en-3-yl-carboxylate

IR: 3070, 2820, 2720, 1735–1710, 1570 $cm^{-1}$.

NMR: 1.41 and 1.61 (2H); 2.78 (1H, t, J=7 Hz); 3.13–3.62 (3H); 3.64 and 3.71 (3H, 2s); 5.95–6.58 (2H); 9.58 and 9.88 (1H, 2s) δ ppm.

SM: m/e=148 (11), 121 (27), 115 (15), 103 (4), 91 (20), 83 (22), 66 (100), 55 (10), 43 (18), 29 (15).

EXAMPLE 3

Methyl 2-formyl-bicyclo[2.2.1]hept-3-yl-carboxylate 4 g (0.022 mole) of methyl 2-formyl-bicyclo[2.2.1]hept-5-en-3-yl-carboxylate—see Example 2 above—in 60 ml of ethyl acetate were hydrogenated in the presence of 100 mg of 10% Pd over charcoal at atmospheric pressure and at room temperature. After absorption (about 1 h) of the theoretical quantity of hydrogen, the reaction mixture was filtered and the clear filtrate was concentrated under reduced pressure. The obtained residue was distilled (pressure: 0.06 Torr/bath temperature: 82°-115°) to yield 3.27 g (yield 82%) of the title compound.

IR: 2820, 2720, 1710–1745 $cm^{-1}$.

NMR: 1.18–1.86 (6H); 2.57–2.98 (3H); 3.15–3.45 (1H); 3.68 and 3.71 (3H, 2s); 9.72 and 9.81 (1H, 2s) δ ppm.

By following the same procedure and by using as starting materials the compounds prepared in accordance with Examples 1 and 2 above, it was possible to synthesize the following saturated corresponding derivatives:

ethyl 2-formyl-bicyclo[2.2.1]hept-3-yl-carboxylate

IR: 2815, 2715, 1710–1740 $cm^{-1}$.

NMR: 1.03–1.80 (6H); 1.26 (3H, t, J=7.5 Hz); 2.58–2.97 (3H); 3.28 (1H, t, J=4.5 Hz); 4.15 and 4.18 (2H, 2q, J=7.5 Hz); 9.71 and 9.80 (1H, s) δ ppm.

n-propyl 2-formyl-bicyclo[2.2.1]hept-3-yl-carboxylate

IR: 2820, 2720, 1715–1740 $cm^{-1}$.

NMR: 0.95 (3H, t, J=7 Hz); 1.17–1.91 (8H); 2.57–3.05 (3H); 3.17–3.42 (1H); 4.05 and 4.08 (2H, t,J=7 Hz); 9.72 and 9.81 (1H, 2s) δ ppm.

isopropyl 2-formyl-bicyclo[2.2.1]hept-3-yl-carboxylate

IR: 2810, 2710, 1710–1735 $cm^{-1}$.

NMR: 1.05–1.87 (6H); 1.21 and 1.22 (6H, 2d, J=7 Hz); 2.50–2.97 (3H); 3.25 (1H, t, J=4.5 Hz); 4.79–5.27 (1H, m); 9.71 and 9.80 (1H, 2s) δ ppm.

n-butyl 2-formyl-bicyclo[2.2.1]hept-3-yl-carboxylate

IR: 2820, 2710, 1715–1740 $cm^{-1}$.

NMR: 0.74–1.13 (3H); 1.16–2.12 (10H); 2.56–3.07 (3H); 3.17–3.42 (1H); 3.97–4.47 (2H); 9.71 and 9.80 (1H, 2s) δ ppm.

sec-butyl 2-formyl-bicyclo[2.2.1]hept-3-yl-carboxylate

IR: 2820, 2720, 1715–1735 $cm^{-1}$.

NMR: 0.91 (3H, t,J=7 Hz); 1.20 and 1.21 (3H, 2d, J=6 Hz); 1.14–1.88 (8H); 2.55–3.08 (3H); 3.10–3.46 (1H); 4.68–5.08 (1H, m); 9.73 and 9.81 (1H, 2s) δ ppm.

n-pentyl 2-formyl-bicyclo[2.2.1]hept-3-yl-carboxylate

IR: 2820, 2720, 1715–1730 $cm^{-1}$.

NMR: 0.91 (3H,J=5 Hz); 1.16–1.98 (12H); 2.55–3.02 (3H); 3.17–3.40 (1H); 3.96–4.28 (2H); 9.72 and 9.81 (1H, 2s) δ ppm.

EXAMPLE 4

Ethyl 5- and 6-methyl-2-formyl-bicyclo[2.2.1]hept-5-en-3-yl-carboxylate 8.0 g (0.11 mole) of dimeric methyl-cyclopentadiene, 14.2 g (0.10 mole) of ethyl 4-oxo-butenoate and 0.1 g of hydroquinone dissolved in 100 ml of toluene were treated according to method B of Example 1 above to give a mixture of ethyl 5-methyl-2-formyl-bicyclo[2.2.1]hept-5-en-3-yl-carboxylate and ethyl 6-methyl-2-formyl-bicyclo[2.2.1]hept-5-en-3-yl-carboxylate.

IR: 3050, 1810, 1710, 1740–1710, 1625 $cm^{-1}$.

NMR: 1.1–1.5 (5H); 1.5–1.9 (3H); 2.65–3.50 (4H); 4.12 and 4.18 (2H, 2qd, J=7 Hz); 5.65 and 5.85 (1H, 2s); 9.58, 9.70 and 9.88 (1H, 3s) δ ppm.

By replacing in the above procedure ethyl 4-oxobutenoate by an homologous ester, the following compounds were obtained:

methyl 5- and 6-methyl-2-formyl-bicyclo[2.2.1]hept-5-en-3-yl-carboxylate

IR: 3050, 2810, 2710, 1710–1740, 1625 $cm^{-1}$.

NMR: 1.3–1.9 (5H, m); 2.6–3.55 (4H, m); 3.65–3.70 (3H, 2s); 5.65 and 5.85 (1H, 2s); 9.58, 9.69 and 9.87 (1H, 3s) δ ppm.

n-propyl 5- and 6-methyl-2-formyl-bicyclo[2.2.1]hept-5-en-3-yl-carboxylate

IR: 3050, 2810, 2710, 1710–1735, 1630 $cm^{-1}$.

NMR: 0.94 (3H, t,J=7 Hz); 1.3–1.9 (7H); 4.1–3.65 (4H); 3.90–4.35 (2H, m); 5.65 and 5.85 (1H); 9.58, 9.70 and 9.88 (1H, 3s) δ ppm.

isopropyl 5- and 6-methyl-2-formyl-bicyclo[2.2.1]hept-5-en-3-yl-carboxylate

IR: 3050, 2810, 2710, 1720–1735, 1625 $cm^{-1}$.

NMR: 1.15–1.65 (8H); 1.70–1.90 (3H, m); 2.60–3.50 (4H); 4.75–5.30 (1H); 5.65 and 5.85 (1H, m); 9.58, 9.70 and 9.90 (1H, 3s) δ ppm.

n-butyl 5- and 6-methyl-2-formyl-bicyclo[2.2.1]hept-5-en-3-yl-carboxylate

IR: 3050, 2810, 2710, 1715–1735, 1625 $cm^{-1}$.

NMR: 0.75–1.10 (3H); 1.20–1.90 (9H); 2.65–3.55 (4H); 3.95–4.25 (2H); 5.65 and 5.85 (1H, 2s); 9.58, 9.70 and 9.85 (1H, 3s) δ ppm.

sec-butyl 5- and 6-methyl-2-formyl-bicyclo[2.2.1]hept-5-en-3-yl-carboxylate

IR: 3050, 2810, 2710, 1715–1735, 1625 $cm^{-1}$.

NMR: 0.9 (3H, T,J=7 Hz); 1.21 (3H, d,J=7 Hz); 1.35–1.88 (6H); 2.0–2.4 (1H); 2.60–3.55 (4H); 4.60–5.15 (1H, m); 5.65 and 5.88 (1H, 2s); 9.58–9.90 (1H) δ ppm.

n-pentyl 5- and 6-méthyl-2-formyl-bicyclo[2.2.1]hept-5-en-3-yl-carboxylate

IR: 3050, 2810, 2710, 1715–1725, 1625 $cm^{-1}$.

NMR: 0.9 (3H, t,J=5 Hz); 1.15–1.90 (11H); 2.65–3.55 (4H); 3.95–4.28 (2H); 5.65 and 5.85 (1H); 9.60, 9.71 and 9.88 (1H, 3s) δ ppm.

EXAMPLE 5

Methyl 5- and 6-methyl-2-formyl-bicyclo[2.2.1]hept-3-yl-carboxylate 3 g of the mixture of methyl 5- and 6-methyl-2-formyl-bicyclo[2.2.1]hept-5-en-3-yl-carboxylate obtained in accordance with Example 4 above were hydrogenated as indicated in Example 3. The title compound was obtained in a 90% yield.

IR: 2810, 2710, 1715–1735 $cm^{-1}$.

NMR: 0.83–1.15 (3H); 1.28–1.82 (4H); 1.84–2.25 (1H); 2.35–3.38 (4H); 3.68 (3H, s); 9.71–10.0 (1H) δ ppm.

In an analogous manner it was possible to prepare the following mixtures of compounds:

ethyl 5- and 6-methyl-2-formyl-bicyclo[2.2.1]hept-3-yl-carboxylate

IR: 2810, 2710, 1710–1735 $cm^{-1}$.

NMR: 0.83–1.83 (6H); 1.24 and 1.26 (3H, 2t, J=7.5 Hz); 1.88–2.33 (2H); 2.38–3.05 (3H); 3.21–3.37 (1H); 4.14 and 4.15 (2H, 2q, J=7.5 Hz); 9.70 to 10.0 (1H) δ ppm.

isopropyl 5- and 6-methyl-2-formyl-bicyclo[2.2.1]hept-3-yl-carboxylate

IR: 2810, 2710, 1715–1730 $cm^{-1}$.

NMR: 0.83–1.65 (12H); 1.85–3.33 (4H); 4.72–5.27 (1H, m); 9.63–10.15 (1H) δ ppm.

EXAMPLE 6

A base perfume composition of "melon" type destined to be incorporated in a deodorizing spray, was prepared by mixing together the following ingredients (parts by weight):

| | |
|---|---|
| ethyl 2-formyl-bicyclo[2.2.1]hept-5-en-3-yl-carboxylate (see Example 1) | 200 |
| α-amylcinnamic alcohol | 200 |
| phenyl-ethyl alcohol | 120 |
| ethyl malonate | 100 |
| trimethyl hexyl acetate | 70 |
| nerol | 60 |
| phenoxyethyl isobutyrate | 40 |
| cis-non-6-en-1-ol 1%* | 40 |
| 2,5-dimethyl-4,5-dihydro-furan-3-ol-4-one[1] 0.1%* | 40 |
| 3-methyl-pentyl isobutyrate | 30 |
| cis-hex-3-en-1-ol 10%* | 20 |
| methyl heptyne-carboxylate 1%* | 20 |
| methyl octyne-carboxylate 1%* | 10 |
| styrallyl acetate | 10 |
| 4-isopropyl-cyclohexyl methanol[2] | 10 |
| pentadecanolide | 10 |
| β-damascenone 1%* | 10 |
| trimethyl-cyclohexene-carbaldehyde 10%* | 5 |
| nonadienol 10%* | 5 |
| Total | 1000 |

*in diethyl phthalate
[1]FURANEOL® (Firmenich SA) - see e.g. British Patent No. 1,476,711)
[2]MAYOL® (Firmenich SA) - see e.g. British Patent No. 1,416,658)

Identical perfuming effects could be obtained by replacing in the above base 200 parts of ethyl 2-formyl-bicyclo[2.2.1]hept-5-en-3-yl-carboxylate by 200 parts of its corresponding n-propyl ester derivative. By replacing the ethyl ester by the same amount of its isopropyl derivative, the fragrance of the composition acquires an odour note of green, aqueous type reminiscent of the odour developed by water-melon.

EXAMPLE 7

A base perfume composition of "bouquet fleuri" type was obtained by mixing together the following ingredients (parts by weight):

| | |
|---|---|
| benzyl salicylate | 100 |
| phenyl ethyl alcohol | 80 |
| dimethyl benzyl carbinol | 80 |
| benzyl acetate | 80 |
| synthetic linalol | 60 |
| heliotropin | 50 |
| hydroxy citronellal | 50 |
| citronellyl acetate | 40 |
| synthetic bulgarian rose | 40 |
| undecylenic aldehyde 10%* | 40 |
| pentadecanolide | 30 |
| α-amyl-cinnamic alcohol | 30 |
| methyl-ionone | 30 |
| α-damascone 10% | 30 |
| menthyl acetate | 20 |
| p-hydroxyphenyl-butan-3-one 10%* | 20 |
| decylic aldehyde 10%* | 20 |
| amyl salicylate | 20 |
| 2,5,9-trimethyl-deca-4,9-dien-1-al 10%* | 20 |
| cyclamen aldehyde | 20 |
| 4-isopropyl-cyclohexylmethanol[1] | 10 |
| linalyl acetate | 10 |

-continued

| | |
|---|---|
| methyl dihydrojasmanate | 10 |
| β-damascenone 1%* | 5 |
| coriander oil | 5 |
| Total | 900 |

*in diethyl phthalate
[1]MAYOL ® (Firmenich SA) - see e.g. British Patent No. 1,416,658)

The above perfume base developed an odour of flowery type of very characteristic nature. This base could be conveniently used for the manufacture of shampoos. By adding to 90 parts of the above base, 10 parts of ethyl 2-formyl-bicyclo[2.2.1]hept-5-en-3-yl-carboxylate, there was obtained a novel composition which presented, beside the mentioned flowery note, a very pleasant fruity, melon top note.

EXAMPLE 8

A base flavouring composition of "melon" type was prepared by mixing the following ingredients (parts by weight:

| | |
|---|---|
| methyl anisate | 5 |
| methyl cinnamate 10%* | 5 |
| phenyl propionic aldehyde 1%* | 5 |
| cyclamen aldehyde 1%* | 10 |
| geraniol 10%* | 10 |
| orange oil | 10 |
| ethyl pelargonate | 15 |
| lemon oil | 25 |
| amyl acetate | 25 |
| ethyl methyl-phenyl-glycidate | 30 |
| amyl isovalerate | 50 |
| amyl butyrate | 50 |
| ethyl isovalerate | 75 |
| ethyl acetyl-acetate | 100 |
| 95% ethanol | 585 |
| Total | 1000 |

*in 95% ethanol

The above base was used for the manufacture of the following flavours (parts by weight), after addition thereto of one of the compounds indicated hereinbelow in the proportion specified:

(1) ethyl 2-formyl-bicyclo[2.2.1]hept-5-en-3-yl-carboxylate (2) isopropyl 2-formyl-bicyclo[2.2.1]hept-5-en-3-yl-carboxylate (3) methyl 2-formyl-bicyclo[2.2.1]hept-5-en-3-yl-carboxylate (4) n-propyl 2-formyl-bicyclo[2.2.1]hept-5-en-3-yl-carboxylate

| | Flavour | | | | |
|---|---|---|---|---|---|
| Compound | A | B | C | D | E |
| (1) | 5 | — | — | — | — |
| (2) | — | 10 | — | — | — |
| (3) | — | — | 10 | — | — |
| (4) | — | — | — | 10 | — |
| Melon Base | 100 | 100 | 100 | 100 | 100 |
| 95% ethanol | 895 | 890 | 890 | 890 | 900 |
| Total | 1000 | 1000 | 1000 | 1000 | 1000 |

Flavour compositions A through E thus prepared were then used for the aromatization of the foodstuffs indicated hereinbelow at the concentration of 100 g of flavour for 100 l of foodstuff or beverage.

Sugar syrup: 650 g of cane-sugar and 10 ml of a 50% aqueous solution of citric acid were dissolved in 1000 ml of water and the flavour compositions were added in the proportions indicated.

Ice-cream: 5 egg yolks and 250 g of sugar were mixed together and 1 lt. of warm milk was added to the mass, while stirring was carried on until a homogeneous onctuous mass was obtained, whereupon the flavour was added. The obtained foodstuff was then cooled.

The flavoured foodstuffs were subjected to the evaluation of a panel of experts who described the effect of the used flavours as follows:

Flavour composition A: more fruity and greener than E, more pronounced juicy character.

Flavour composition B: typically melon.

Flavour composition C: flavour note of green fruit type more pronounced than E.

Flavour composition D: more fruity than E, reminiscent of excessively ripe melon.

What we claim is:

1. A compound of formula

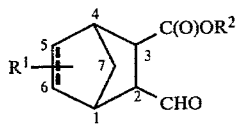

(I)

containing a single or a double bond in the position indicated by the dotted lines and wherein symbol $R^1$ represents a hydrogen atom or a methyl radical and $R^2$ defines a linear or branched alkyl radical containing 1 to 6 carbon atoms, with the proviso however that $R^1$ cannot represent hydrogen when $R^2$ represents a methyl radical.

2. Ethyl 2-formyl-bicyclo[2.2.1]hept-5-en-3-yl-carboxylate.

3. n-Propyl 2-formyl-bicycl[2.2.1]hept-5-en-3-yl-carboxylate.

* * * * *